United States Patent
Bharat et al.

(10) Patent No.: US 11,653,893 B2
(45) Date of Patent: May 23, 2023

(54) 3D TRACKING OF AN INTERVENTIONAL INSTRUMENT IN 2D ULTRASOUND GUIDED INTERVENTIONS

(71) Applicant: KONINKLIJKE PHILIPS N.V., Eindhoven (NL)

(72) Inventors: Shyam Bharat, Arlington, MA (US); Ameet Kumar Jain, Boston, MA (US); Antonio Bonillas Vaca, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 541 days.

(21) Appl. No.: 16/098,992

(22) PCT Filed: Apr. 27, 2017

(86) PCT No.: PCT/EP2017/060019
§ 371 (c)(1),
(2) Date: Nov. 5, 2018

(87) PCT Pub. No.: WO2017/194314
PCT Pub. Date: Nov. 16, 2017

(65) Prior Publication Data
US 2019/0159752 A1 May 30, 2019

Related U.S. Application Data

(60) Provisional application No. 62/334,006, filed on May 10, 2016.

(51) Int. Cl.
*A61B 8/08* (2006.01)
*A61B 8/00* (2006.01)
(Continued)

(52) U.S. Cl.
CPC .............. *A61B 8/0841* (2013.01); *A61B 8/12* (2013.01); *A61B 8/4254* (2013.01); *A61B 8/466* (2013.01);
(Continued)

(58) Field of Classification Search
CPC ....... A61B 8/0841; A61B 34/20; A61B 90/11; A61B 8/12; A61B 8/4254; A61B 8/466;
(Continued)

(56) References Cited

U.S. PATENT DOCUMENTS 5,469,848 A * 11/1995 Toleman ................. A61B 8/10
600/452
6,019,724 A * 2/2000 Gronningsaeter ... A61B 8/0833
600/439
(Continued)

FOREIGN PATENT DOCUMENTS

WO 2011138698 A1 11/2011
WO WO-2015010900 A1 * 1/2015 ............ A61M 25/04
(Continued)

OTHER PUBLICATIONS

Sensor-Works, "How Do Piezoelectric Sensors Work?", 2020 (Year: 2020).*
(Continued)

*Primary Examiner* — Katherine L Fernandez
*Assistant Examiner* — Brooke Lyn Klein

(57) ABSTRACT

An interventional instrument (30) having ultrasound sensors (S1, S2, S3, S4, . . . ) is tracked using an ultrasound imaging device (10) that acquires and displays a 2D ultrasound image of a visualization plane (18), and performs 2D ultrasound sweeps for a range of plane angles (θ) obtained by rotating the ultrasound probe (12) and encompassing the visualization plane angle. For each ultrasound sensor, an optimal plane is found based on its emitted signal strength over the
(Continued)

range of plane angles, and the ultrasound sensor is located in its optimal plane by analyzing the sensor signal as a function of the timing of the beams fired by the ultrasound probe. These locations in their respective optimal planes are transformed to a 3D reference space using a transform (42) parameterized by plane angle, and a visual indicator is displayed of spatial information (T, L) for the interventional instrument generated from the locations of the one or more ultrasound sensors in the 3D reference space.

17 Claims, 7 Drawing Sheets

(51) Int. Cl.
*A61B 90/11* (2016.01)
*A61B 8/12* (2006.01)
*A61B 34/20* (2016.01)
*A61B 90/00* (2016.01)
*A61B 17/34* (2006.01)
*A61B 17/00* (2006.01)
*G01S 15/89* (2006.01)

(52) U.S. Cl.
CPC .............. *A61B 34/20* (2016.02); *A61B 90/11* (2016.02); *A61B 2017/00274* (2013.01); *A61B 2017/3413* (2013.01); *A61B 2034/2051* (2016.02); *A61B 2034/2055* (2016.02); *A61B 2034/2059* (2016.02); *A61B 2034/2063* (2016.02); *A61B 2090/367* (2016.02); *A61B 2090/3929* (2016.02); *A61B 2090/3983* (2016.02); *G01S 15/894* (2013.01)

(58) Field of Classification Search
CPC .... A61B 2034/2051; A61B 2034/2055; A61B 2034/2059; A61B 2034/2063; A61B 2090/2367; A61B 2090/3929; A61B 2090/3983; A61B 2017/00274; A61B 2017/3413; G01S 15/894
See application file for complete search history.

(56) References Cited

U.S. PATENT DOCUMENTS

| | | | |
|---|---|---|---|
| 9,895,133 B2 | 2/2018 | Pagoulatos et al. | |
| 2003/0060700 A1 | 3/2003 | Solf et al. | |
| 2008/0119727 A1* | 5/2008 | Barbagli | A61B 8/0833 600/424 |
| 2008/0186378 A1* | 8/2008 | Shen | G06T 7/38 348/65 |
| 2009/0093715 A1* | 4/2009 | Downey | A61B 8/463 600/437 |
| 2009/0306509 A1* | 12/2009 | Pedersen | G01S 15/8936 600/446 |
| 2010/0137715 A1* | 6/2010 | Kakee | G01S 7/52087 600/443 |
| 2010/0298705 A1* | 11/2010 | Pelissier | A61B 8/4254 600/443 |
| 2012/0155723 A1* | 6/2012 | Deno | A61B 8/0883 382/128 |
| 2013/0261432 A1 | 10/2013 | Guo et al. | |
| 2013/0274608 A1 | 10/2013 | Takeda et al. | |
| 2013/0289393 A1 | 10/2013 | Kruecker et al. | |
| 2014/0024928 A1 | 1/2014 | Boctor et al. | |
| 2016/0180528 A1* | 6/2016 | Reynolds | A61B 6/032 382/128 |
| 2016/0199668 A1 | 7/2016 | Bharat | |
| 2017/0020558 A1* | 1/2017 | Xu | A61B 8/483 |

FOREIGN PATENT DOCUMENTS

| | | | | |
|---|---|---|---|---|
| WO | WO-2015039995 A1 * | 3/2015 | | A61B 90/37 |
| WO | 2015101913 A1 | 7/2015 | | |
| WO | 2015116584 A1 | 8/2015 | | |
| WO | 2016009350 A1 | 1/2016 | | |
| WO | 2016010900 A1 | 1/2016 | | |

OTHER PUBLICATIONS

Kruecker, J. et al., "Fusion of transrectal ultrasound with pre-acquired MRI for prostate biopsy guidance", MEDICAMUNDI 52/1 2008/07 at pp. 25-31 (2008).

Guo, X. et al., "Active Ultrasound Pattern Injection System (AUSPIS) for Interventional Tool Guidance", Plos ONE, Oct. 2014, vol. 9, issue 10, e104262, p. 1-13.

* cited by examiner

| Time | Needle tracking data | Probe tracking data |
|---|---|---|
| $T_1$ | | $\theta_1$ |
| $T_2$ | | $\theta_2$ |
| $T_3$ | | $\theta_3$ |
| $T_4$ | $(X_1, Y_1)$ | $c_4\theta_3 + d_4\theta_4$ |
| $T_5$ | $(a_4X_1 + b_4X_2, a_4Y_1 + b_4Y_2)$ | $\theta_4$ |
| $T_6$ | $(a_5X_1 + b_5X_2, a_5Y_1 + b_5Y_2)$ | $\theta_5$ |
| $T_7$ | $(X_2, Y_2)$ | $\theta_6$ |
| $T_8$ | $(a_7X_2 + b_7X_3, a_7Y_2 + b_7Y_3)$ | $c_8\theta_6 + d_8\theta_7$ |
| $T_9$ | $(X_3, Y_3)$ | $\theta_7$ |
| $T_{10}$ | $(a_9X_3 + b_9X_4, a_9Y_3 + b_9Y_4)$ | $\theta_8$ |
| $T_{11}$ | $(a_{10}X_3 + b_{10}X_4, a_{10}Y_3 + b_{10}Y_4)$ | $\theta_9$ |
| $T_{12}$ | $(X_4, Y_4)$ | $\theta_{10}$ |
| $T_{13}$ | $(a_{12}X_4 + b_{12}X_5, a_{12}Y_4 + b_{12}Y_5)$ | $\theta_{11}$ |
| $T_{14}$ | $(a_{13}X_4 + b_{13}X_5, a_{13}Y_4 + b_{13}Y_5)$ | $\theta_{12}$ |
| | $(X_5, Y_5)$ | |

FIG. 5

| Time | Needle tracking data | Probe tracking data |
|---|---|---|
| $T_1$ | | $\theta_1$ |
| $T_2$ | | $\theta_2$ |
| $T_3$ | $(X_1, Y_1)$ | $\theta_3$ |
| $T_4$ | $(X_1, Y_1)$ | $\theta_3$ |
| $T_5$ | $(X_1, Y_1)$ | $\theta_4$ |
| $T_6$ | $(X_2, Y_2)$ | $\theta_5$ |
| $T_7$ | $(X_2, Y_2)$ | $\theta_6$ |
| $T_8$ | $(X_3, Y_3)$ | $\theta_6$ |
| $T_9$ | $(X_3, Y_3)$ | $\theta_7$ |
| $T_{10}$ | $(X_3, Y_3)$ | $\theta_8$ |
| $T_{11}$ | $(X_4, Y_4)$ | $\theta_9$ |
| $T_{12}$ | $(X_4, Y_4)$ | $\theta_{10}$ |
| $T_{13}$ | $(X_4, Y_4)$ | $\theta_{11}$ |
| $T_{14}$ | $(X_5, Y_5)$ | $\theta_{12}$ |
| $T_{15}$ | $(X_5, Y_5)$ | $\theta_{13}$ |

FIG. 6

3D TRACKING OF AN INTERVENTIONAL INSTRUMENT IN 2D ULTRASOUND GUIDED INTERVENTIONS

CROSS-REFERENCE TO PRIOR APPLICATIONS

This application is the U.S. National Phase application under 35 U.S.C. § 371 of International Application Serial No. PCT/EP2017/060019, filed on Apr. 27, 2017, which claims the benefit of U.S. Patent Application No. 62/334,006, filed on May 10, 2016. This application is hereby incorporated by reference herein.

FIELD

The following relates generally to the medical arts, ultrasound-guided interventional procedure arts, prostate biopsy arts, and the like.

BACKGROUND

Ultrasound-guided interventional procedures, such as biopsies, brachytherapy seed implantation, cryoablation, laser ablation, or so forth, utilize ultrasound imaging to guide the interventional instrument to the target tissue. For example, in a transperineal prostate intervention, ultrasound imaging using a transrectal ultrasound (TRUS) probe, typically along with a guidance grid abutted against the perineum, is used to guide the needle insertion. The ultrasound imaging performed during the interventional procedure is usually two-dimensional (2D) imaging. To contextualize the 2D ultrasound images, a pre-acquired three-dimensional (3D)-TRUS ultrasound image and/or a 3D magnetic resonance (MR) image of the target region may be used (Kruecker et al., "Fusion of transrectal ultrasound with pre-acquired MRI for prostate biopsy guidance", MEDICA-MUNDI 52/1 2008/July at pages 25-31 (2008)). However, instrument contrast in ultrasound is usually poor, with intermittent instrument visibility, leading to the so-called "invisible tool" phenomenon.

To address poor instrument contrast in ultrasound, dedicated ultrasound sensors may be mounted on the interventional instrument (Mung et al., "Tool Tracking for Ultrasound-Guided Interventions", G. Fichtinger, A. Martel, and T. Peters (Eds.): MICCAI 2011, Part I, LNCS 6891, pp. 153-60 (2011)). In one approach, the sensor serves as an active ultrasound transponder by re-radiating received ultrasound pulses. In another approach, the sensor outputs a voltage when the ultrasound signal is received. In either approach, the knowledge of the combination of the direction of the ultrasound beam that sonicates the sensor and the time interval between ultrasound pulse emission and the sensor response ("time of flight") enables localization of the sensor. If this approach is used with real-time 3D-TRUS ultrasound imaging, then localization in the three-dimensional space is achievable.

However, in practice a 2D ultrasound is more commonly employed for live guidance during needle insertion. 2D ultrasound is faster, can be performed using a lower cost ultrasound transducer array, and the 2D image is readily displayed on a video display component of the ultrasound device display. More particularly, in transperineal prostate biopsy procedures, a pre-procedurally acquired 3D MR data set is used to delineate the target from where the biopsy sample will be taken. At the beginning of the biopsy procedure, a 3D-TRUS image set is acquired by scanning the TRUS probe manually from prostate base to apex (or by rotating the probe about an axis parallel to its own, from left lateral to right lateral extremes of the prostate (or vice versa), while imaging in sagittal orientation) and reconstructed from 2D TRUS image frames and the 3D-TRUS is registered to the previously acquired MR data set. Thereafter, the TRUS probe is used to acquire 2D images at the sagittal orientation (for a prostate procedure), for example using conventional brightness or B-mode imaging, to provide live 2D guidance as the biopsy needle is inserted. The TRUS probe is tracked using electromagnetic (EM) or some other TRUS probe spatial tracking technology, and the live 2D ultrasound images are thereby linked to the corresponding frame of the reconstructed 3D TRUS image, and therefore, to the MR data set, from the TRUS-MR registration.

SUMMARY

In one disclosed aspect, a tracking device is disclosed for tracking an interventional instrument that has one or more ultrasound sensors disposed with the interventional instrument. The tracking device comprises an ultrasound imaging device including an ultrasound probe configured to acquire a two-dimensional (2D) ultrasound image, and an electronic processor. The electronic processor is programmed to operate the ultrasound imaging device to perform an interventional instrument tracking method including: operating the ultrasound imaging device to display a 2D ultrasound image of a visualization plane; performing 2D ultrasound sweeps of a plurality of planes that encompasses the visualization plane and, for each 2D ultrasound plane of the plurality of planes, detecting a signal emitted by each ultrasound sensor in response to the 2D ultrasound sweep of the plane; for each ultrasound sensor, identifying an optimal plane of the plurality of planes for which the detected signal emitted by the ultrasound sensor is highest and identifying the location of the ultrasound sensor in the optimal plane, and identifying the location of the ultrasound sensor in a three dimensional (3D) reference space based on the location of the ultrasound sensor in the optimal plane and knowledge of how the optimal plane relates to the 3D space (e.g., 3D TRUS/MRI); and determining spatial information for the interventional instrument, including at least one of tip location and orientation of the interventional instrument, based on the identified locations of the one or more ultrasound sensors in the 3D reference space. The location of the ultrasound sensor in the optimal plane may be identified, for example, based on analyzing the sensor signal as a function of the timing of the beams fired by the ultrasound probe.

In another disclosed aspect, a tracking method is disclosed for tracking an interventional instrument that has one or more ultrasound sensors disposed with the interventional instrument. The tracking method comprises: operating an ultrasound imaging device including an ultrasound probe to display a two dimensional (2D) ultrasound image of a visualization plane; rotating the ultrasound probe about an axis to scan a plurality of planes spanning a range of plane angles that encompasses the plane angle of the visualization plane and, for each plane of the plurality of planes, operating the ultrasound imaging device to perform a 2D ultrasound sweep of the plane; during each 2D ultrasound sweep, detecting a signal emitted by each ultrasound sensor in response to the 2D ultrasound sweep; for each ultrasound sensor, identifying an optimal plane for which the signal emitted by the ultrasound sensor is highest and locating the ultrasound sensor in the optimal plane; determining the location of each ultrasound sensor in a three dimensional (3D) reference space by transforming the location of the ultrasound sensor in its optimal plane to the 3D reference space using a transform parameterized by plane angle; determining spatial information for the interventional instrument based on the locations of the one or more ultrasound sensors in the 3D reference space; and displaying a visual indicator of the determined spatial information for the interventional instrument on the displayed 2D ultrasound image of the visualization plane.

In another disclosed aspect, a tracking device is disclosed for tracking an interventional instrument that has one or more ultrasound sensors disposed with the interventional instrument. The tracking device comprises an ultrasound imaging device including an electronic processor and a display, and an ultrasound probe operatively connectable with the ultrasound imaging device and rotatable under control of the ultrasound imaging device to acquire a two dimensional ultrasound image at a plane defined by a plane angle. The ultrasound imaging device is programmed to: acquire and display a 2D ultrasound image of a visualization plane defined by a visualization plane angle; perform 2D ultrasound sweeps for a range of plane angles encompassing the visualization plane angle and, for each 2D ultrasound sweep, storing its plane angle and a signal emitted by each ultrasound sensor in response to the 2D ultrasound sweep; identify an optimal plane for each ultrasound sensor based on its emitted signal strength over the range of plane angles and locating the ultrasound sensor in its optimal plane by analyzing the sensor signal as a function of the timing of the beams fired by the ultrasound probe during the 2D ultrasound sweep of the optimal plane; transform the locations of the ultrasound sensors in their respective optimal planes to a three dimensional (3D) reference space using a 2D to 3D transform parameterized by plane angle; and display, on the displayed 2D ultrasound image, a visual indicator of spatial information for the interventional instrument generated from the locations of the one or more ultrasound sensors in the 3D reference space.

One advantage resides in providing three-dimensional interventional instrument information using 2D live ultrasound imaging during an interventional procedure.

Another advantage resides in providing more accurate and reliable interventional instrument tracking during an interventional procedure.

Another advantage resides in providing the foregoing advantages without the cost of providing ultrasound imaging and transrectal ultrasound (TRUS) probe hardware capable of performing live 3D ultrasound imaging.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 5 illustrates a suitable approach for synchronizing data streams by interpolation.

FIG. 6 illustrates a suitable approach for synchronizing data streams by data persistence.

DETAILED DESCRIPTION

Figure 1:
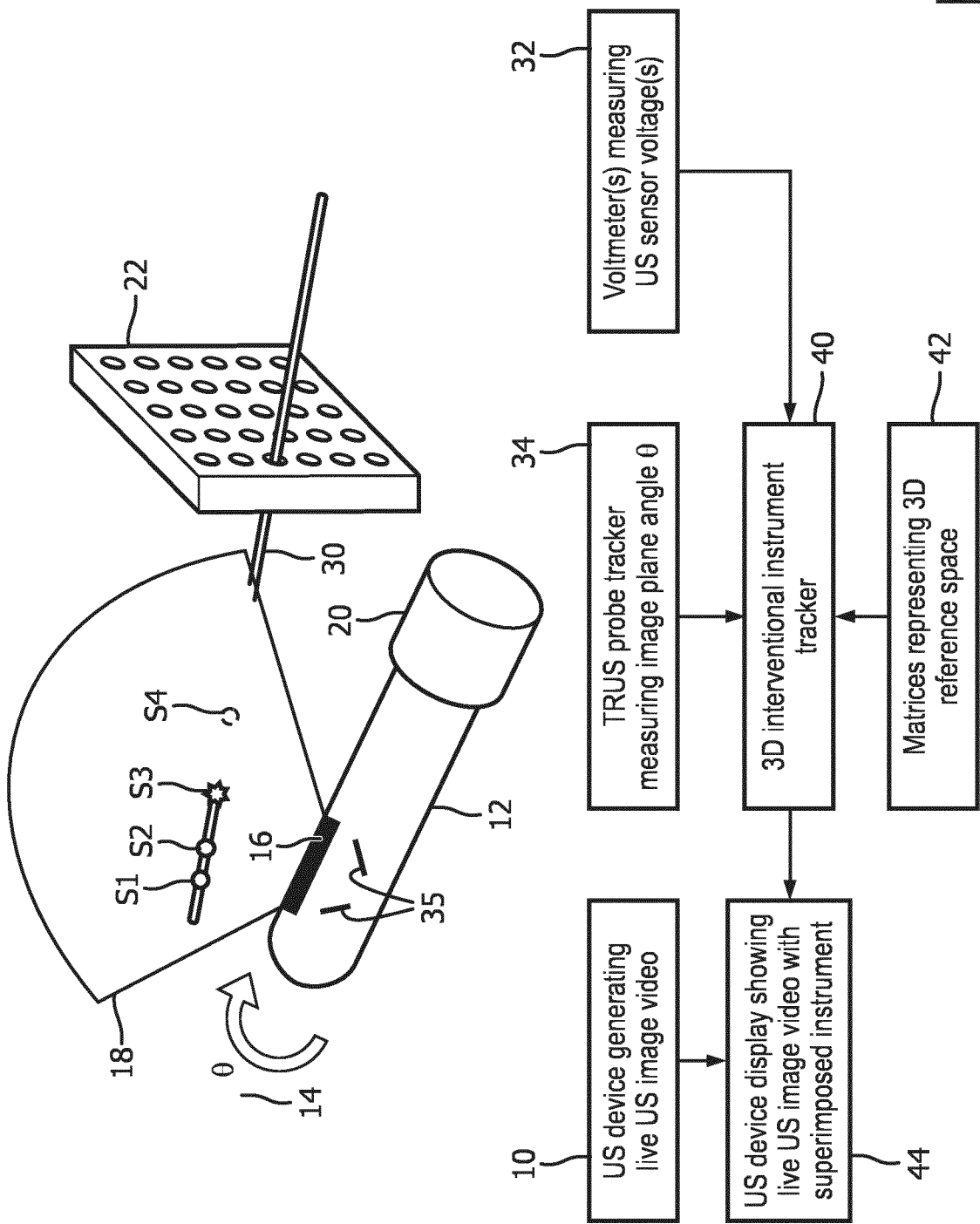
FIG. 1 diagrammatically shows a transrectal ultrasound (TRUS) probe, its two-dimensional (2D) image plane, an interventional instrument (illustrative biopsy needle) with ultrasound sensors disposed at pre-determined locations along the instrument, and a guidance grid for guiding the interventional instrument, with selected measured parameters including TRUS probe rotational angle indicated.

As described above, while pre-procedural MR images and/or reconstructed 3D TRUS images provide 3D context for planning a transperineal intervention, 2D TRUS images are often used for live guidance during needle insertion. In a typical orientation, the sagittal ultrasound array of the probe is used in the live guidance. In view of this, the imaged plane is sometimes referred to as a "sagittal" plane. However, it is to be understood that this sagittal plane is with respect to the sagittal array of the TRUS probe, and is not necessarily aligned with the sagittal plane of the patient. For example, the TRUS probe may be rotated about its axis, and the procedure is still deemed to be under "sagittal image guidance", even though the imaged sagittal plane may be rotated or tilted respective to the sagittal plane of the patient. The terms "sagittal plane", "sagittal image guidance", and the like are to be understood as being used herein in this sense, i.e. the sagittal plane is the plane imaged using the sagittal array of the TRUS probe.

Use of 2D-TRUS imaging as the live guidance tool implicitly assumes that the needle lies in the sagittal plane imaged by the TRUS probe. However, due to anatomical constraints during needle insertion and needle-tissue interaction, it is generally not possible to ensure that the needle lies completely in the sagittal visualization plane during insertion, and in practice a given sagittal image usually contains only a portion of the needle. This leads to positional error and poor visibility of needles, and both degradation mechanisms increase with increasing deviation of the needle away from the ultrasound visualization plane. The needle is effectively "projected" onto the sagittal visualization plane, and the surgeon is not informed as to the 3D position and orientation of the needle in the body.

These problems could be overcome by performing 3D ultrasound imaging. However, this approach has substantial disadvantages, including potentially increased ultrasound imaging equipment cost and more complex (and potentially confusing) live visualization in the 3D image space. Typically, the surgeon is most comfortable viewing the conventional two-dimensional sagittal plane, rather than attempting to visualize the needle position in a 3D perspective or otherwise-displayed three-dimensional space representation.

Interventional instrument tracking devices and methods disclosed herein advantageously retain the conventional approach of sagittal plane visualization via 2D ultrasound imaging, with the modification that the ability to rotate the TRUS probe about its axis is leveraged to extract additional three-dimensional information. While described with illustrative reference to transperineal prostate intervention using a TRUS probe, the disclosed approaches are readily employed in ultrasound-guided interventions directed to other anatomy such as the liver and/or for performing other procedures such as brachytherapy seed implantation, cryoablation, laser ablation, or so forth.

With reference to FIG. 1, an ultrasound-guided intervention system includes an ultrasound imaging device 10 operatively connected with an ultrasound probe 12 (for example using a suitable connecting cable and mating connectors). In the illustrative example, the ultrasound probe is a transrectal ultrasound (TRUS) probe 12 sized and shaped for insertion into the rectum of a patient. Such a TRUS probe is commonly used for performing transperineal prostate intervention. The TRUS probe 12 is generally cylindrical and as such has a defined axis 14. An ultrasound transducer array 16 is located on a sidewall of the cylindrical TRUS probe 12, so as to perform sonication and imaging of a two-dimensional (2D) image plane 18. A stepper device such as a cable, fitting or other mechanical component that can be moved manually or a stepper device such as a stepper motor 20 can be operated to automatically rotate the TRUS probe 12 about the axis 14, for example under control of an electronic processor (e.g. microprocessor or microcontroller) of the ultrasound imaging device 10 (although a separate electronic processor performing this control is alternatively contemplated). In an alternative embodiment, the stepper motor 20 is omitted, the stepper device is not motorized, and instead the TRUS probe 12 is rotated manually by the surgeon or other surgical team member. Rotation of the TRUS probe 12 about the axis 14 revolves the ultrasound transducer array 16 about the axis 14, and hence the image plane can be rotated to a chosen angle, which is designated herein without loss of generality as the (image) plane angle θ.

For the illustrative example of a transperineal prostate intervention procedure, live guidance during needle insertion usually employs ultrasound imaging of the sagittal plane. Accordingly, in the examples herein the visualization plane is designated as the sagittal plane and, for convenience, is designated as θ=0°. It will be appreciated that other interventional procedures may employ a different visualization plane appropriate for the position and orientation of the ultrasound probe used to guide the interventional procedure.

Transperineal prostate intervention also commonly utilizes a guidance grid 22 positioned abutting against the perineum of the prostate patient (not shown), and an interventional instrument 30 (e.g., a biopsy needle) is guided through an entry point of the guidance grid 22. Use of the optional guidance grid 22 provides a convenient tool for systematically sampling a region of the prostate by successively inserting the biopsy needle 30 through designated entry points of the grid 22. It will be appreciated that in other ultrasound-guided interventions, the grid 22 may not be used, or if used may be positioned against some other portion of the anatomy depending upon the target tissue or organ.

The interventional instrument 30 includes one or more ultrasound sensors disposed with the interventional instrument; without loss of generality, the illustrative example includes four such ultrasound sensors S1, S2, S3, S4; however, the number of sensors can be one, two, three, the illustrative four, five, or more. In this context, the term "disposed with" encompasses ultrasound sensors disposed on a surface of the instrument 30, or disposed sensors disposed inside the instrument 30, e.g. embedded within the instrument 30. Each ultrasound sensor S1, S2, S3, S4 emits a signal in response to sonication by an ultrasound beam from the ultrasound transducer array 16. The illustrative ultrasound sensors S1, S2, S3, S4 are piezoelectric sensors that generate an electrical signal (e.g. a voltage) in response to sonication. Such sensors suitably comprise a piezoelectric material such as a composite film of lead zirconate titanate (PZT) and polyvinylidene fluoride (PVDF) copolymers, although substantially any biocompatible material exhibiting sufficiently strong piezoelectric effect may be used, e.g. with electrodes for extracting the electric signal response. Each piezoelectric sensor S1, S2, S3, S4 suitably includes electrical leads/traces (not shown), e.g. secured to or disposed with (i.e. on or in) the needle 30, to carry the piezoelectric sensor voltage off the interventional instrument 30. Alternatively, a micro-radio transmitter may be integrated with the piezoelectric sensor to wirelessly output the sensor voltage. In alternative embodiments (not illustrated), the ultrasound sensors may be ultrasound-reflective sensors that re-radiate received ultrasound pulses, in which case the sensor signal is the re-radiated ultrasound pulse which may be received by the same ultrasound transducer array 16 that sonicates the ultrasound-reflective sensors.

It is to be appreciated that the disclosed components, e.g. the ultrasound probe 12 with its stepper motor 20, and the interventional instrument 30, are merely illustrative examples, and other hardware configurations implementing desired functionality may be employed. For example, the stepper motor may be located elsewhere and operatively connected with the TRUS probe 12 via a driveshaft and optional gearing. In other procedures, the ultrasound probe may be other than the illustrative TRUS probe 12.

Figure 2:
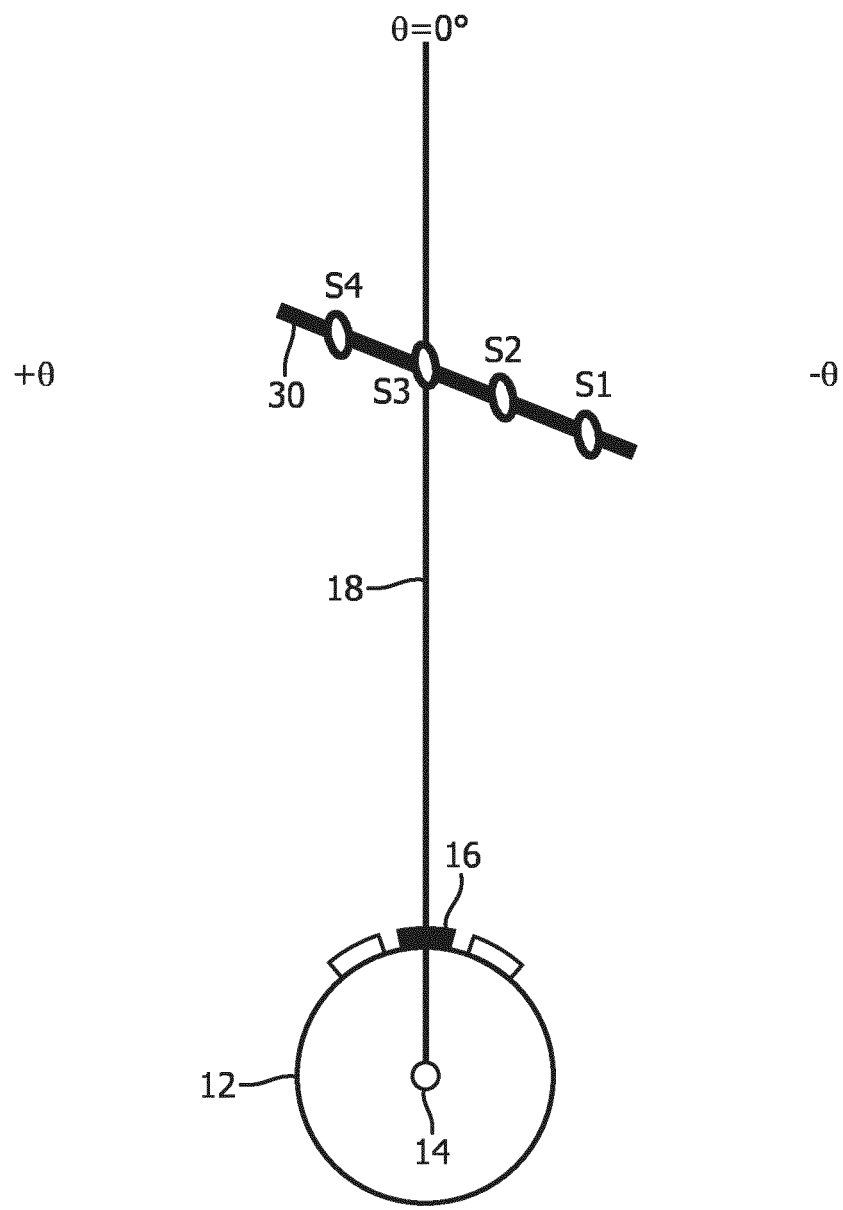
FIG. 2 diagrammatically shows the TRUS probe of FIG. 1 viewed along the axis designated in FIG. 1, with the visualization plane with designated angle $\theta=0°$ indicated along with two additional image planes accessed by rotating the TRUS probe over a positive or negative angle, respectively, indicated in grayed dashed lines.

With continuing reference to FIG. 1 and with brief reference to FIG. 2, for 2D ultrasound imaging a linear array of ultrasound transducers 16, or more generally an array of ultrasound transducers 16 with a generally linear form factor, are typically used. Such a transducer array with linear form factor is conveniently mounted on the side of a generally cylindrical probe body, so that the disclosed approach of rotating the ultrasound probe about an axis (e.g. the cylinder axis) is generally applicable to many interventional procedures employing 2D ultrasound guidance. FIG. 2 shows an "end" view of the TRUS probe 12, looking down the axis 14, to illustrate how rotating the TRUS probe 12 away from the visualization plane (angle θ=0°) 18 to a positive angle, or alternatively to a negative angle, results in probing 2D imaging planes that are tilted compared with the θ=0° visualization plane 18. In general, the imaging planes probed by such rotation contain (or pass close to) the rotational axis 14 (although the illustrative axis 14 is outside of the visualized portion of the image plane since it is "behind" the transducer array 16).

As seen in FIG. 2, the biopsy needle 30 does not (in general) lie precisely in the visualization plane 18. As a result, of the four ultrasound sensors S1, S2, S3, S4, only one sensor S3 lies in the visualization plane 18. Two sensors S1, S2 lie at negative angles (−θ) relative to the visualization plane 18. One sensor S4 lies at positive angle (+θ) relative to the visualization plane 18. In FIG. 1, this is diagrammatically shown by having the portion of the needle 30 lying "behind" the visualization plane 18 as viewed from the perspective of FIG. 1 shown in dashed lines. This includes the sensor S4.

The sensor S3 lying in the visualization plane 18 can be localized as follows. The ultrasound probe 12 performs a 2D ultrasound sweep of the plane 18. During this sweep, the ultrasound beam is swept across the 2D plane 18 and, at some point, this beam intersects and sonicates the sensor S3. In response, the piezoelectric sensor S3 emits a sensor voltage that is detected. A voltmeter 32 detects this voltage output by the ultrasound sensor S3. (More generally, the piezoelectric sensor may output some other electric signal such as a change in capacitance or an electric current, and an electric signal detector detects the electric signal emitted by the piezoelectric sensor in response to the 2D ultrasound sweep). The detected sensor signal is time stamped. The location of the ultrasound sensor S3 in the visualization plane 18 can be determined based on time-of-flight and ultrasound beam angle information derived from the ultrasound scanner 10. In this case, the time of flight corresponds to the time interval between emission of the ultrasound beam pulse and detection of the sensor voltage. This time, multiplied by the speed of sound in the prostate tissue, provides the distance from the ultrasound transducer 16. This distance along with the ultrasound beam angle localizes the sensor S3 in the plane 18. (Note that if ultrasound-reflective sensors are used then the time-of-flight is the echo time interval between ultrasound pulse emission and detection of the re-emission in this case, the time interval times the speed of sound is two times the distance from the ultrasound transducer to the reflective sensor, and so a factor of 0.5 is applied). The skilled artisan will recognize that this 2D localization approach is similar to that employed in 2D brightness mode (b-mode) imaging, except that the response signal is due to the sensor rather than ultrasound reflection from imaged tissue.

Such a 2D localization approach might also detect the out-of-plane sensors S1, S2, and S4, if the elevational ultrasound beam spread is such that it also partially sonicates these sensors. In this case, the sensor signal responsive to the ultrasound beam will be weaker due to the partial sonication; if the sensor is too far outside of the plane 18 then it may not be sonicated at all leading to sensor "invisibility". It will also be appreciated that the out-of-plane sensor, if sonicated, will be erroneously localized in the plane 18 (since it is assumed to lie in the plane) at the distance given by the time-of-flight. This positional error becomes larger with increasing distance of the sensor away from the visualization plane 18.

With continuing reference to FIG. 1, in embodiments disclosed herein, this error is corrected by the following approach implemented by a three-dimensional (3D) interventional instrument tracker 40 (e.g., in some implementations embodied by suitable programming of the microprocessor or microcontroller of the ultrasound imaging device 10 to control the transducer array 16 and stepper motor 20, and reading the voltmeter 32, to perform the disclosed approach). Instead of performing a single 2D ultrasound sweep of the single plane 18, 2D ultrasound sweeps of a plurality of planes are performed. The various plane angles θ are reached via operation of the stepper motor 20. The chosen plurality of planes encompasses (but does not necessarily include) the visualization plane 18. For each 2D ultrasound sweep, a sensor signal emitted by each ultrasound sensor S1, S2, S3, S4 in response to the 2D ultrasound sweep is detected. (In some cases the detected sensor signal may be a null signal, i.e. if the sensor is too far out of the plane of the 2D sweep then the detected sensor signal is zero). For each ultrasound sensor, an optimal plane is identified, from amongst the plurality of planes, for which the sensor signal emitted by the ultrasound sensor is highest. For this optimal plane, the ultrasound sensor is located using the time-of-flight and ultrasound beam angle information as already described for sensor S3. (In the case of sensor S3, the optimal plane is the visualization plane 18 since sensor S3 lies in this plane 18). Then, the location of each ultrasound sensor S1, S2, S3, S4 is determined in a three dimensional (3D) reference space by transforming the location of each ultrasound sensor in its optimal plane to the 3D reference space. This is suitably done using a transform 42 parameterized by plane angle θ. Spatial information for the interventional instrument 30 (e.g. tip position and orientation) are determined based on the locations of the one or more ultrasound sensors S1, S2, S3, S4 in the 3D reference space. In performing this transformation, position of the ultrasound probe 12 and particularly the angle θ may be monitored by the TRUS probe tracker 34; alternatively, the angle may be determined from rotational encoding of the stepper motor 20. A visual indicator of the determined spatial information for the interventional instrument (e.g., its tip position and/or a line indicating its orientation) is displayed on a display 44 of the ultrasound device 10, e.g. superimposed on or otherwise displayed with a displayed 2D ultrasound image of the visualization plane (e.g. b-mode ultrasound video). Alternatively, the 3D orientation of the needle 30 may be displayed in a pre-acquired and reconstructed 3D-TRUS image, or in a pre-acquired and reconstructed 3D MRI data set. It is also contemplated for the spatial information to include a prediction of the needle trajectory, e.g. by extending the current needle orientation.

The ultrasound probe tracker 34 tracks the position and orientation of the ultrasound probe 12 respective to the 3D reference space. The probe tracker 34 may employ any suitable probe tracking technology. For example, the probe tracker 34 may employ electromagnetic tracking and comprise an electromagnetic (EM) field generator and illustrative EM sensors 35 disposed with (e.g. on or in) the ultrasound probe 12. Alternatively, the probe tracker may employ optical tracking technology that detects optical reflectors or LEDs disposed with (on or in) the ultrasound probe, or may employ a robotic encoder comprising a multi jointed arm with spatial encoding joints, or so forth.

In summary, during needle insertion the TRUS probe 12 is rotated by a stepper device, e.g. by the stepper motor 20, with the range of rotation of the image plane encompassing all the sensors S1, S2, S3, S4 on the needle 30. An optimal plane is identified for each sensor and its location in that optimal plane is determined. These locations are then transformed to a 3D reference space using a transform of the 2D location parameterized by the plane angle θ. The needle is preferably held stationary during probe rotation. In one approach, there can be 'start' and 'stop' buttons on the user interface, which the user can click to indicate the beginning and end of data acquisition during the probe rotation. The following quantities are acquired during the probe rotation: sensor voltages; 2D tracked sensor estimates in the plane of the 2D sweep based on time-of-flight and sonication beam angle in the 2D plane; and rotational positions (angles θ) of the TRUS probe. Each of these quantities (or each sample of these quantities) is time stamped. Interpolation may be employed to synchronize the data samples of the 2D positions and the angles θ.

Typically, it is not desired to have an ultrasound sensor positioned at the tip of the interventional instrument 30, since this tip usually includes or embodies functional apparatus for performing a biopsy, ablation procedure, or the like. Accordingly, in a suitable approach the sensors S1, S2, S3, S4 have pre-determined (i.e. known) positions along the needle 30, and the position of the tip relative to these known positions of the sensors is also pre-determined (known) and can therefore be obtained from the tracked 3D positions of the sensors S1, S2, S3, S4 on the needle 30. In general, at least two ultrasound sensors along the needle 30 are needed to determine its orientation; however, if the guidance grid 22 is used then the second position for determining orientation may be a pre-determined (known) entry point of the guidance grid 22 through which the interventional instrument 30 is guided.

Figure 3:
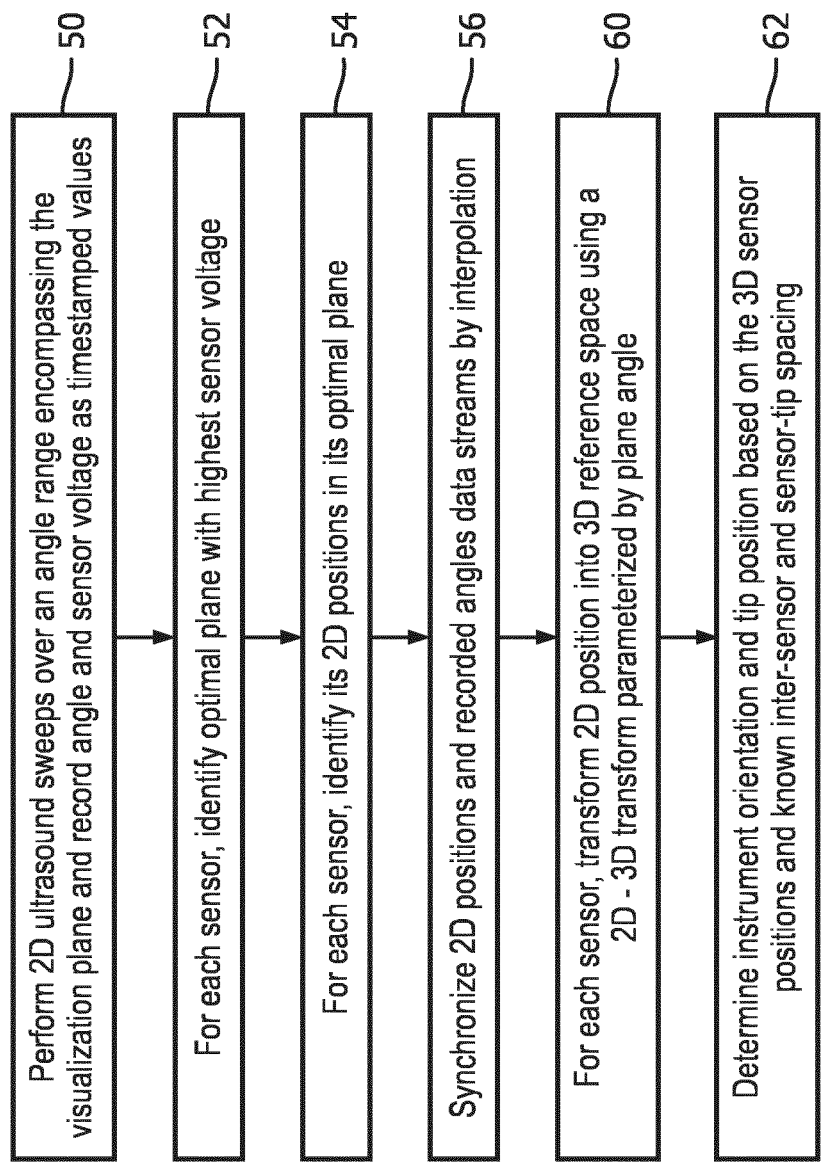
FIG. 3 diagrammatically shows an illustrative method for determination of the interventional instrument tip and orientation using the device of FIG. 1.

With reference to FIG. 3, an illustrative method for determination of the interventional instrument tip and orientation using the device of FIG. 1 is described. In an operation 50, the 2D ultrasound sweeps are performed over an angle range encompassing the visualization plane 18, and the plane angle θ and sensor voltages are recorded as time stamped values. The angle range is also preferably selected to encompass the likely positions of most, or all, of the ultrasound sensors S1, S2, S3, S4 on the needle 30.

Figure 4:
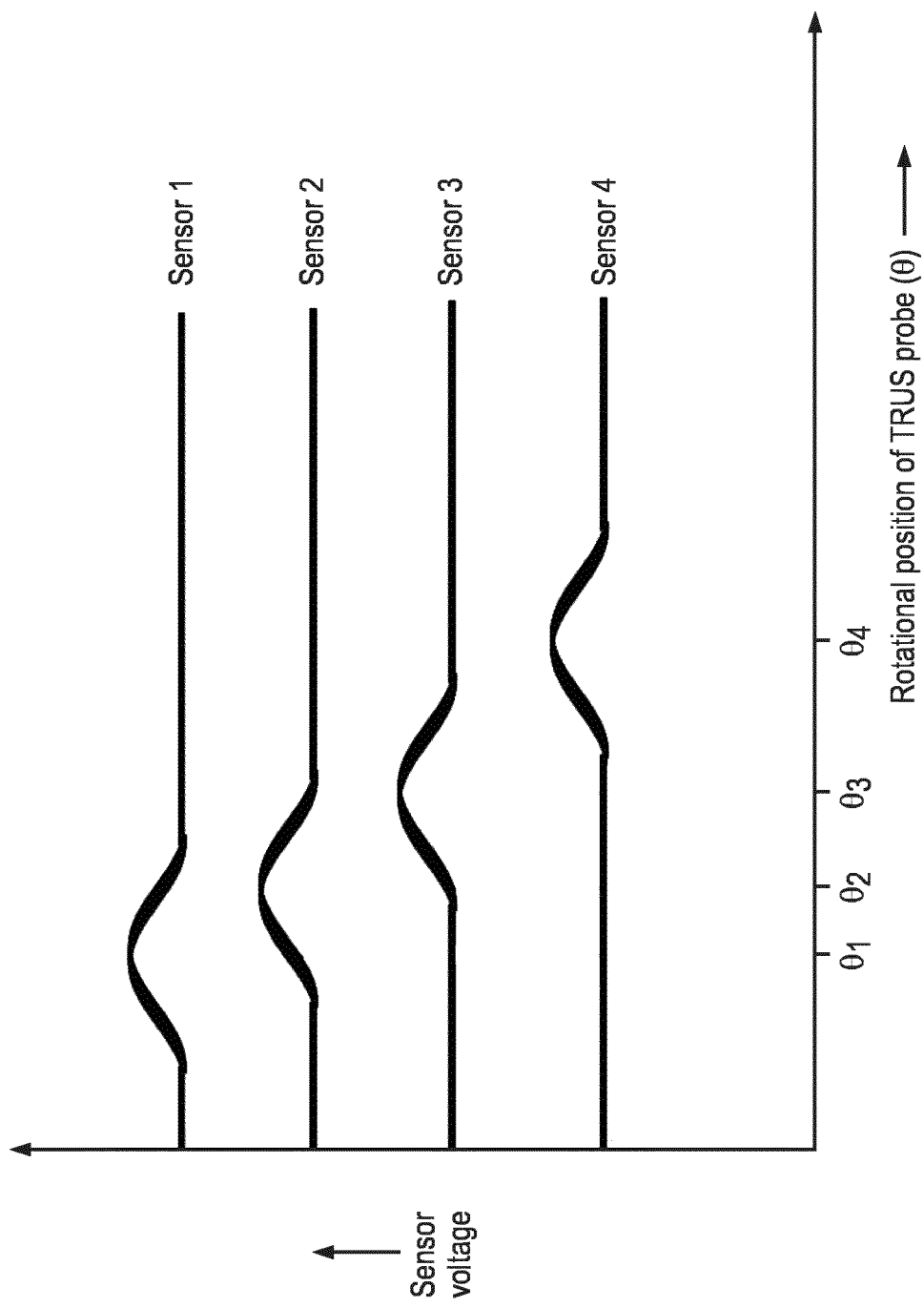
FIG. 4 diagrammatically plots ultrasound sensor voltage as a function of angle ($\theta$) of the TRUS probe for four sensors disposed at spaced-apart positions along a portion of the length of the interventional instrument.

With continuing reference to FIG. 3 and with further reference to FIG. 4, in an operation 52 an optimal plane is identified for each sensor. This optimal plane is the plane for which the 2D ultrasound sweep yielded the largest sensor signal. FIG. 4 illustrates this operation 52 by plotting sensor voltage as a function of plane angle θ (i.e. rotational position of the TRUS probe 12). Note that FIG. 4 plots the sensors with different arbitrary voltage offsets so that the four curves for the four sensors S1, S2, S3, S4 are spaced apart. For each sensor, a peak is observed in its voltage-vs-angle plot, and the plane angle corresponding to this peak is the optimal plane angle (and hence indexes the optimal plane) for that sensor. Note that for the example of FIGS. 1 and 2 the sensor S3 lies in the visualization plane 18, so that the angle $\theta_3=0$ for this example. With continuing reference to FIG. 3, in an operation 54 the 2D position of each sensor in its optimal plane is determined. This may be done using the time-of-flight and ultrasound beam angle information collected for the sensor in its optimal plane during the 2D ultrasound sweep of its optimal plane.

At this point, there are two pieces of information that have been collected for each sensor: its optimal plane (θ), and its 2D position in that optimal plane, denoted herein as p(x, y). In the illustrative example, these two pieces of information come from different sources: the optimal plane is measured by the TRUS probe tracker 34; whereas the position p(x, y) in that plane is determined using the ultrasound device 10 and the voltmeter 32. These values are synchronized in an operation 56, for example by interpolation. In one suitable synchronization approach, data streams are acquired and stored in a common computer (e.g. the electronics of the ultrasound imaging device 10). Hence, the system clock can be used to regulate/interpret the data. Persistence or interpolation is used to "fill in" missing data from the data stream acquired at a lower acquisition rate (usually this is p(x, y)) and is then temporally matched to the data stream captured at a higher frame rate (usually the TRUS probe angle θ). The synchronized data streams can then be combined to estimate the 3D orientation of the needle.

With brief reference to FIG. 5, an illustrative interpolation approach for performing the synchronization operation 56 is described. FIG. 5 shows time stamps (column labeled "Time"), 2D sensor positions (column labeled "Needle tracking data"), and plane angle θ (column labeled "Probe tracking data"). To illustrate the interpolation consider that at time instant $T_4$, there are missing entries in both the needle tracking and probe tracking data. The missing data may be interpolated using a weighted average of the data immediately preceding and succeeding the current time point $T_4$. For the needle tracking data, this amounts to interpolating $(X_1,Y_1)$ and $(X_2,Y_2)$, such as: $(a_4X_1+b_4X_2, a_4Y_1+b_4Y_2)$, where possible values for the weights $a_4$ and $b_4$ are: $a_4=(T_6-T_4)/(T_6-T_3)$ and $b_4=(T_4-T_3)/(T_6-T_3)$. Similarly, $c_4=(T_5-T_4)/(T_5-T_3)$ and $d_4=(T_4-T_3)/(T_5-T_3)$. Note that this method must be implemented with some time lag, since it utilizes data before and after the missing entry for the interpolation.

With brief reference to FIG. 6, in an alternative embodiment for performing the synchronization operation 56, the latest data can be persisted until the next data point for that stream arrives. This technique can be performed in real-time without any time lag, but may suffer from slightly reduced accuracy as compared with the interpolation approach of FIG. 5.

With returning reference to FIG. 3, in an operation 60 the 2D position of each sensor is transformed to the 3D reference space using the 2D-3D transformation(s) 42 which is parameterized by the plane angle θ. By "parameterized" it is meant that the transformation(s) 42 is dependent on the plane angle θ, or in other words the transform 42 operates to identify the location P(x, y, z) of the ultrasound sensor in the 3D reference space according to $P(x, y, z)=T_{probe,\theta} \times p(x, y)$, where $T_{probe,\theta}$ is the transformation 42 and p(x, y) is the location in the optimal plane. The precise formulation of the transformation 42 depends upon the selection, or definition, of the 3D reference space In one embodiment, the transformation 42 is as follows:

$$P(x,y,z)=T_{EM,\theta}^{FG} \times T_{US}^{EM} \times p(x,y)$$

where $T_{US}^{EM}$ is the transformation from the optimal 2D-US image plane to the EM sensors 35 attached to the ultrasound probe 12 (available from the US probe calibration of the EM tracking system). The US probe calibration is typically independent of the probe position and is a pre-computed registration matrix. The other transform $T_{EM,\theta}^{FG}$ is the transformation from the EM sensors 35 on the ultrasound probe 12 to the EM field generator (FG) of the TRUS probe tracker 34, which establishes the 3D reference space coordinate system. This transformation $T_{EM,\theta}^{FG}$ is a function of the optimal plane angle θ. More generally, if another probe tracking technology is used, then the transformation $T_{EM,\theta}^{FG}$ is replaced by a suitable transformation into the 3D reference space coordinate system of that tracker.

Figure 7:
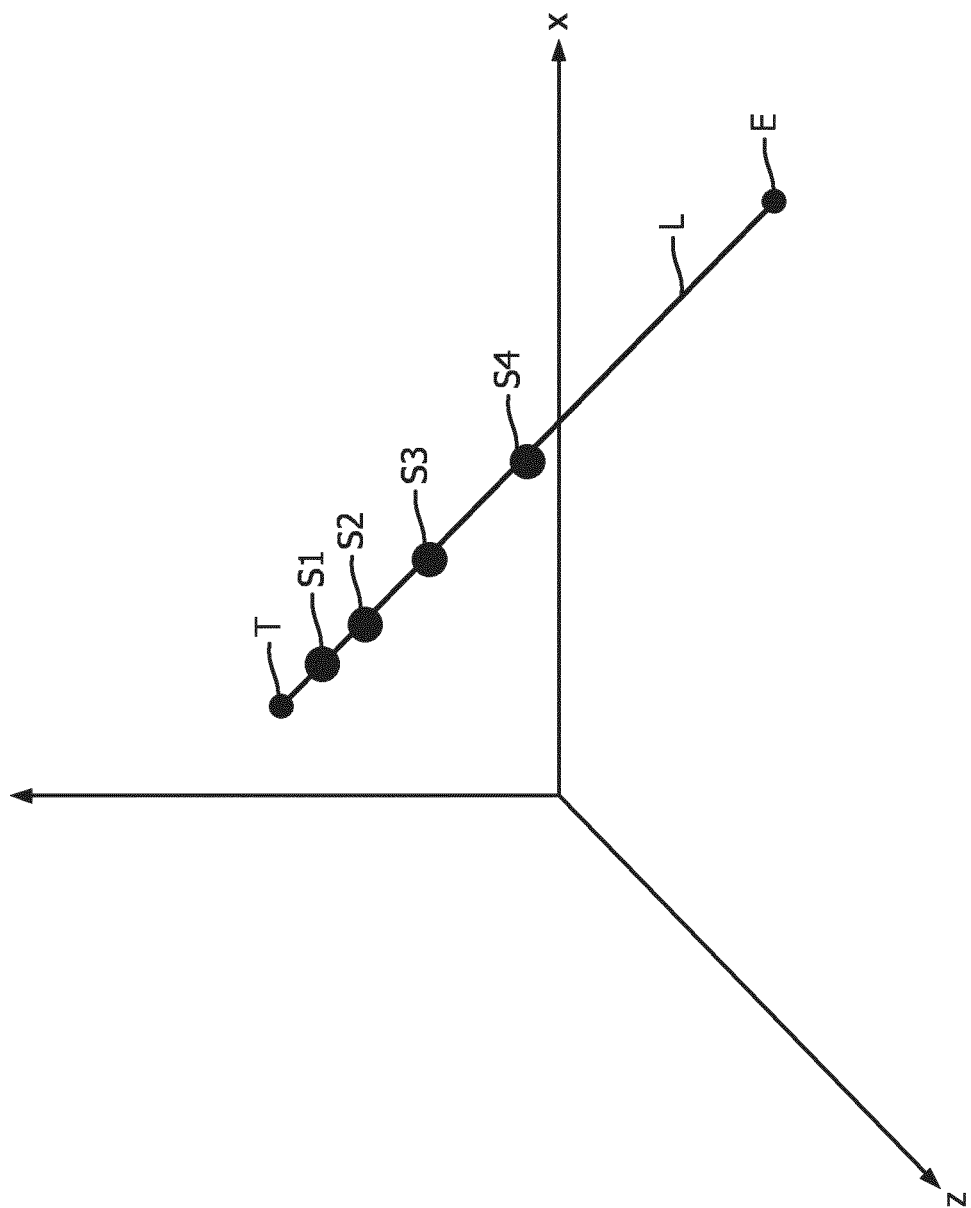
FIG. 7 diagrammatically illustrates determination of the interventional instrument tip and orientation based on determined 3D positions of the ultrasound sensors disposed at spaced-apart positions along a portion of the length of the interventional instrument, and optionally further based on the known entry point of the interventional instrument in the guidance grid.

With continuing reference to FIG. 3 and with further reference to FIG. 7, in an operation 62 spatial information for the interventional instrument 30 (e.g. its tip position and orientation) is determined based on the 3D sensor positions P(x, y, z) and known inter-sensor and sensor-tip spacings. In one variant embodiment, this is also based on the pre-determined (known) entry point of the guidance grid 22 through which the interventional instrument 30 is guided. FIG. 7 illustrates this approach by illustrating the 3D reference space with the locations P(x, y, z) of each sensor S1, S2, S3, S4 plotted. The entry point of the guidance grid 22 through which the interventional instrument 30 is guided is also plotted as a point E. The orientation of the needle 30 is then plotted as a line L passing through these points, suitably determined by linear regression. A tip position T of the tip of the interventional instrument 30 is suitably determined by the known tip-to-sensor spacings for the four sensors S1, S2, S3, S4 measured along the best-fit line L. The tip position determined from the tip-to-sensor distance for each of the four sensors S1, S2, S3, S4 may be averaged to provide greater accuracy.

In the illustrative embodiments, the stepper motor 20 is configured to rotate the ultrasound probe 12 about its axis 14. In another contemplated embodiment, the stepper motor is configured to translate an ultrasound probe along a linear direction transverse to the 2D visualization plane (i.e. along a normal to the visualization plane), in which case the plurality of planes that encompasses the visualization plane is a set of parallel planes.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A tracking system comprising:
    an interventional instrument having one or more ultrasound sensors;
    an ultrasound imaging device including an ultrasound probe configured to acquire a two-dimensional (2D) ultrasound image, wherein a plurality of tracking sensors are disposed on the ultrasound probe;
    an ultrasound probe tracker configured to track position and orientation of the ultrasound probe based on the plurality of tracking sensors, wherein a three-dimensional (3D) reference space is defined with respect to the ultrasound probe tracker; and
    an electronic processor programmed to operate the ultrasound imaging device to perform tracking of the interventional instrument, the electronic processor configured to:
        operate the ultrasound imaging device to display a 2D ultrasound image of a visualization plane;
        operate the ultrasound imaging device to rotate the ultrasound probe to perform a plurality of 2D ultrasound sweeps over a range of plane angles encompassing the visualization plane;
        receive, from the ultrasound probe tracker, a tracked rotational position of the ultrasound probe corresponding to each of the plane angles;
        derive a 2D -to-3D transform based on pre-computed registration information of the plurality of tracking sensors disposed on the ultrasound probe and the 3-D reference space;
        for each ultrasound sensor of the one or more ultrasound sensors:
            for each plane angle of the range of plane angles, detect a signal emitted by the ultrasound sensor in response to a 2D ultrasound sweep of the plurality of 2D ultrasound sweeps at the plane angle,
            analyze the detected signal emitted by the ultrasound sensor for each plane angle to select a plane angle for which the detected signal emitted by the ultrasound sensor has a highest signal strength,
            identify a location of the ultrasound sensor, in a selected 2D plane corresponding to the selected plane angle, as a time stamped sample,
            identify a parameter of the selected 2D plane as a time stamped sample,
            synchronize, with reference to a common system clock, the time stamped sample of the location of the ultrasound sensor in the selected 2D plane and the time stamped sample of the parameter of the selected 2D plane by interpolation, and
            transform the location of the ultrasound sensor in the selected 2D plane to the 3D reference space using the 2D-to-3D transform as a function of the selected plane angle, the identified location of the ultrasound sensor in the selected 2D plane, and the corresponding tracked rotational position of the ultrasound probe from the ultrasound probe tracker; and
        determine spatial information for the interventional instrument, including at least one of tip location and orientation of the interventional instrument during a medical procedure, based on the transformed location of each of the one or more ultrasound sensors in the 3D reference space.

2. The tracking system of claim 1, further comprising a stepper device configured to rotate the ultrasound probe about an axis to perform the plurality of 2D ultrasound sweeps and to acquire the 2D ultrasound image at a plane having a plane angle in the range of plane angles controlled by the stepper device.

3. The tracking system of claim 1, wherein the location $P(x, y, z)$ of the ultrasound sensor in the 3D reference space is identified as $P(x, y, z) = T_{probe,\theta} \times p(x, y)$, where $p(x, y)$ is the location of the ultrasound sensor in the selected 2D plane and $T_{probe,\theta}$ is the 2D-to-3D transform from the selected plane to the 3D reference space.

4. The tracking system of claim 1, wherein the one or more ultrasound sensors of the interventional instrument are piezoelectric sensors.

5. The tracking system of claim 1, wherein the one or more ultrasound sensors of the interventional instrument are ultrasound-reflective sensors that re-radiate a received ultrasound pulse and the electronic processor is further programmed to detect the re-radiated ultrasound pulse emitted by each of the one or more ultrasound sensors in response to the 2D ultrasound sweep.

6. The tracking system of claim 1, wherein the electronic processor is further programmed to, for each ultrasound sensor of the one or more ultrasound sensors, identify the location of the ultrasound sensor in the selected plane based on analyzing the detected signal as a function of timing of beams fired by the ultrasound probe.

7. The tracking system of claim 1, wherein the electronic processor is further programmed to display a visual indicator of the determined spatial information for the interventional instrument on the displayed 2D ultrasound image of the visualization plane.

8. The tracking system of claim 1, wherein:
    the signals emitted by the ultrasound sensor in response to the plurality of 2D ultrasound sweeps are voltage generated by the ultrasound sensor,
    the ultrasound imaging device includes a voltmeter that measures the voltage generated by the ultrasound sensor, and
    the detected signal emitted with the highest signal strength is the detected signal emitted with the highest voltage.

9. The tracking system of claim 1, wherein:
    the plurality of tracking sensors disposed on the ultrasound probe includes at least one electromagnetic (EM) sensor, and the ultrasound probe tracker has an EM field generator that detects the at least one EM sensor to track the ultrasound probe, wherein the 3D reference space is defined with respect to the EM field generator; or the plurality of tracking sensors disposed on the ultrasound probe has includes at least one optical reflector, and the ultrasound probe tracker has a detector that detects the at least one optical reflector to track the ultrasound probe.

10. The tracking system of claim 2, wherein the ultrasound probe is a transrectal ultrasound probe.

11. The tracking system of claim 2, further comprising:
a guidance grid configured to be positioned abutting against a perineum and to guide the interventional instrument through an entry point of the guidance grid,
wherein the electronic processor is further programmed to determine the spatial information for the interventional instrument further based on a location in the 3D reference space of the entry point of the guidance grid through which the interventional instrument is guided.

12. A method for tracking an interventional instrument that has one or more ultrasound sensors disposed on the interventional instrument, the tracking method comprising:
operating an ultrasound imaging device, including an ultrasound probe, to display a two-dimensional (2D) ultrasound image of a visualization plane;
operating the ultrasound imaging device to rotate the ultrasound probe to perform a plurality of 2D ultrasound sweeps over a range of plane angles encompassing the visualization plane, wherein a plurality of tracking sensors are disposed on the ultrasound probe;
receiving a tracked rotational position of the ultrasound probe from an ultrasound probe tracker configured to track position and orientation of the ultrasound probe based on the plurality of tracking sensors, wherein a three-dimensional (3D) reference space is defined with respect to the ultrasound probe tracker;
derive a 2D-to-3D transform based on pre-computed registration information of the plurality of tracking sensors disposed on the ultrasound probe and the 3-D reference space,
for each ultrasound sensor of the one or more ultrasound sensors:
for each plane angle of the range of plane angles, detecting a signal emitted by the ultrasound sensor in response to a 2D ultrasound sweep of the plurality of 2D ultrasound sweeps at the plane angle,
analyzing the detected signal emitted by the ultrasound sensor for each plane angle to select a plane angle for which the detected signal emitted by the ultrasound sensor has a highest signal strength,
identifying a location of the ultrasound sensor in a selected 2D plane corresponding to the selected plane angle,
generating a time stamped sample of the selected plane angle using the ultrasound probe tracker,
assigning a time stamp to the location of the ultrasound sensor in the selected 2D plane,
synchronizing, with reference to a common system clock, the time stamped location of the ultrasound sensor in the selected 2D plane and the time stamped sample of the selected plane angle by interpolation, and
transforming the location of the ultrasound sensor in the selected plane to the 3D reference space using the 2D-to-3D transform as a function of the selected plane angle, the identified location of the ultrasound sensor in the selected 2D plane, and the corresponding tracked rotational position of the ultrasound probe from the ultrasound probe tracker;
determining spatial information for the interventional instrument during a medical procedure based on the location of each of the one or more ultrasound sensors in the 3D reference space; and
displaying a visual indicator of the determined spatial information for the interventional instrument on the displayed 2D ultrasound image of the visualization plane.

13. The tracking method of claim 12, wherein the ultrasound probe is a transrectal ultrasound probe and the visualization plane is a sagittal plane of the transrectal ultrasound probe.

14. The tracking method of claim 12, wherein the one or more ultrasound sensors disposed on the interventional instrument are piezoelectric sensors and the operation of detecting a signal emitted by each ultrasound sensor in response to the 2D ultrasound sweep includes detecting a sensor voltage generated by the ultrasound sensor in response to the 2D ultrasound sweep.

15. The tracking method of claim 12, wherein locating the ultrasound sensor in the selected plane is based on analyzing the signal as a function of timing of beams fired by the ultrasound probe.

16. The tracking method of claim 13, wherein the spatial information for the interventional instrument is determined further based on a location in the 3D reference space at which the interventional instrument passes through a guidance grid.

17. The tracking system of claim 9, wherein:
the location (x, y, z) of the ultrasound sensor in the 3D reference space is identified as $P(x, y, z) = T_{EM,\theta}^{FG} \times T_{US}^{EM} \times p(x, y)$, where $p(x, y)$ is the location of the ultrasound sensor in the selected 2D plane; and $T_{EM,\theta}^{FG}$ and $T_{U}^{EM}$ comprise the 2D-to-3D transform; wherein $T_{EM,\theta}^{FG}$ is a transformation from the selected plane to the at least one EM sensor disposed on the ultrasound probe; and $T_{US}^{EM}$ is a transformation from the at least one EM sensor disposed on the ultrasound probe to the EM field generator of the ultrasound probe tracker that is a function of the selected plane angle.

* * * * *